United States Patent [19]
Shaffner

[11] Patent Number: 5,980,573
[45] Date of Patent: Nov. 9, 1999

[54] METHOD AND APPARATUS FOR FIGHTING INFECTION AND MAINTAINING JOINT SPACING IN A PROSTHESIS IMPLANT AREA

[76] Inventor: Richard L. Shaffner, 1624 Manhasset Farm Rd., Dunwoody, Ga. 30338

[21] Appl. No.: 08/854,445

[22] Filed: May 12, 1997

[51] Int. Cl.⁶ .............................. A61F 2/32; A61F 2/02; A61F 2/34; A61F 2/36
[52] U.S. Cl. .............................. 623/22; 623/23; 623/11; 606/99; 606/100
[58] Field of Search .............................. 623/22, 23, 11; 606/99, 100

[56] References Cited

U.S. PATENT DOCUMENTS

| | | | |
|---|---|---|---|
| 4,516,277 | 5/1985 | Butel | 3/1.913 |
| 4,851,007 | 7/1989 | Gray | 623/23 |
| 4,919,666 | 4/1990 | Buchhorn et al. | 623/16 |
| 4,919,679 | 4/1990 | Averill et al. | 606/100 |
| 5,133,771 | 7/1992 | Duncan et al. | 623/23 |
| 5,370,698 | 12/1994 | Heimke et al. | 623/18 |
| 5,681,286 | 10/1997 | Wilcox et al. | 623/22 |

Primary Examiner—Paul B. Prebilic
Assistant Examiner—Choon P. Koh
Attorney, Agent, or Firm—Thomas, Kayden, Horstemeyer & Risley

[57] ABSTRACT

A temporary non-weight bearing prosthesis to be placed inside an implant area of a joint replacement patient. The prosthesis is impregnated with an antibiotic agent which leaches out to the surrounding tissue to fight infection in the implant area. While the infection is being overcome, the prosthesis maintains the joint spacing of the implant area against the contractive force of the surrounding muscles and tendons by fully occupying the space in which a primary prosthesis had once been.

10 Claims, 4 Drawing Sheets

METHOD AND APPARATUS FOR FIGHTING INFECTION AND MAINTAINING JOINT SPACING IN A PROSTHESIS IMPLANT AREA

FIELD OF THE INVENTION

The present invention generally relates to a method and apparatus for fighting infection and maintaining joint spacing in a prosthesis implant area of joint replacement patients. More particularly, the present invention relates to a temporary non-weight bearing prosthesis which includes a cementitious substance such as polymethylmethacrylate impregnated with an antibiotic agent which will leach out of the polymethylmethacrylate to fight infection in the implant area. The invention further relates to a method of forming and inserting the temporary non-weight bearing prosthesis into the implant area of the patient such that the joint spacing of the patient will be maintained until the time at which a primary prosthesis can be implanted.

BACKGROUND OF THE INVENTION

Bodily infection is a major concern for patients having implanted structures such as total knee or total hip replacements. In that any object implanted into the human body is a foreign object, regardless of the duration of time it has existed within the body, infection originating from even remote areas of the body can cause complications with the implanted object. For example, if the patient were to become infected from a rusted nail, the infection would likely spread to the tissue surrounding a joint implant.

Several different procedures have been developed in the past to prevent the formation and spread of infection in an implant area. One such procedure has been to administer large doses of antibiotics to the patient in hopes of eradicating the infection all together. Although this procedure is very simple and straightforward, it unfortunately rarely cures the patient of the infection by itself.

A more effective solution has been to remove the implant and to replace it with some form of spacer containing an antibiotic agent. For example, in the case of total knee replacement patients, physicians will remove the femoral and tibial prostheses and the polyethylene "meniscus" positioned therebetween and replace them with a puck-shaped spacer made of bone cement impregnated with an antibiotic. Typically, the spacer is formed during the operation on a side table in the operating room so that the surgeon can first inspect the joint to determine what size spacer will be needed. After the appropriate size has been ascertained, the surgeon or an assistant simply mixes the constituent elements of the bone cement, typically a polymer and a monomer that will form polymethyimethacrylate, and adds an appropriate amount of antibiotic, typically in powder form. Once the bone cement begins to harden, it becomes malleable and may be shaped by hand to fit within the implant area of the patient where the primary prosthesis had once been. When the spacer has adequately hardened, it is then inserted into the implant area and the incision closed in the conventional manner.

Positioned in the implant area, the antibiotic is slowly leached out from the bone cement and into the surrounding tissue to prevent the formation and spread of the infection.

While the infection is being fought, typically over a period of 4 to 6 weeks, the bone cement spacer maintains the amount of joint spacing that was present in the implant area prior to removal of the primary prosthesis. If some form of spacer were not placed in the implant area, this joint spacing would be substantially reduced due to the contraction of the muscles and tendons of the patient during the recuperation period.

Antibiotic-impregnated bone cement has also been utilized to prevent the formation and spread of infection in total hip replacement patients. In this scenario, the acetabular cup and the hip stem of the primary hip prosthesis are first removed. Next, the surgeon mixes the polymer, monomer, and the antibiotic agent and forms small beads of bone cement. These beads of bone cement are then positioned in a spaced relationship along a length of stainless steel suture wire. Once the bone cement has adequately hardened, the wire together with the beads is inserted into the femoral canal to destroy any infection present within the femur. After the infection has been overcome, the surgeon withdraws the beads of bone cement by simply pulling the suture wire out of the femoral canal, carefully counting the number of beads removed to ensure that no beads remain in the femur.

Unlike the knee spacer, the bead and suture wire device does not maintain the joint spacing of the implant area since the device does not occupy any of the acetabular cavity that the head and the acetabular cup of the primary hip prosthesis previously occupied. Since the joint will be immobilized and the patient often bedridden for a substantial period of time, contraction of the unused muscles and tendons can cause substantial joint spacing shrinkage. Although this shrinkage is not in itself harmful to the patient, it will shorten the patient's limb requiring the patient to either walk with a limp or use some form of orthotic device to compensate for the shortened limb. While it is sometimes possible for the physician to stretch the muscles and tendons of the patient to restore some of this lost spacing, it is unlikely that the patient will regain the full amount of joint spacing he or she had before the primary hip prosthesis was removed.

Accordingly, it can be seen that it would be desirable to provide a method and apparatus for fighting infection in an implant area of a patient which also maintains adequate joint spacing.

SUMMARY OF THE INVENTION

Briefly stated, the present invention comprises a method and apparatus for fighting infection and maintaining adequate joint spacing in an implant area. In one embodiment, a pre-formed temporary hip prosthesis is provided which may be inserted by the surgeon into the implant area after a primary prosthesis has been removed. The temporary hip prosthesis includes an elongated stem portion for insertion into the femoral canal, and a head portion for placement in the acetabular cavity. Connecting the head portion to the elongated stem portion is a neck portion. Each of the elongated stem portion, neck portion, and head portion are formed from a material impregnated with an antibiotic agent. Typically, this material will be a polymeric bone cement such as polymethylmethacrylate ("PMMA"). Fabricated in this manner, the antibiotic agent within the bone cement will leach out over time to the surrounding tissue to prevent the formation and spread of infection within the implant area. Concurrently, the temporary hip prosthesis will maintain adequate joint spacing in the implant area against the compressive forces of the surrounding bones due to contracting muscles and tendons.

Typically, the neck portion of the pre-formed temporary hip prosthesis will include a collar adapted to abut a top surface of the femur to limit the depth of insertion of the elongated stem into the femoral canal. The pre-formed temporary hip prosthesis may also include an elongated canal which extends from an upper proximal end to a lower distal end of the elongated stem portion. When so provided, the elongated canal permits the insertion of an elongated removal tool which can finely engage the lower distal end of the elongated stem portion and can be used to pull the temporary hip prosthesis out from the femoral canal. Alternatively or additionally, the temporary hip prosthesis may include a threaded aperture formed in the upper proximal end of the elongated stem portion. This threaded aperture is adapted to accept a like-threaded removal tool which, when threaded into the aperture, may be used to pull the pre-formed temporary hip prosthesis from the femoral canal.

In an alternative embodiment, a prosthesis frame is provided which may be used to form a temporary prosthesis. In situations involving hip stem replacement patients, the prosthesis frame typically includes an elongated stem portion, a neck portion, and a head portion. In the preferred embodiment, the elongated stem portion is provided with a plurality of radial flanges and the head portion is provided with arcuate flange members. Both the radial flanges and the arcuate flange members form recesses which may be filled with a hardenable material impregnated with an antibiotic agent. Thus, the prosthesis frame functions as an endoskeleton for supporting the surrounding bone cement. Preferably, bone cement such as PMMA will be used in that it is approved by the United States Food and Drug Administration ("FDA") for insertion into the body.

In use, the surgeon or his or her assistant will select an appropriately sized prosthesis frame and fill the recesses provided on the stem and head portions to the extent at which the bone cement is flush with the outer edges of the radial flanges and arcuate flange members such that a temporary hip prosthesis is formed having a substantially cylindrical shank and a bulbous head. Once the bone cement has adequately hardened, the newly formed temporary hip prosthesis is ready for insertion.

Typically, the prosthesis frame, like the hardenable material, will be composed of bone cement since new cement bonds well with hardened bone cement. Similar to the pre-formed temporary hip prosthesis described above, the elongated stem portion of the prosthesis frame will typically be provided with an elongated canal which extends therethrough and/or a threaded aperture formed its upper proximal end to facilitate removal of the temporary hip prosthesis once the infection has been overcome.

The present invention also comprises a method for preventing the spread of infection while simultaneously maintaining joint spacing in an implant area. In one method, the surgeon examines the patient to determine the size and extent of the joint spacing of a hip prosthesis implant area. Once the size has been ascertained, the surgeon selects an appropriately sized pre-formed temporary hip prosthesis formed from a material containing an antibiotic agent, typically PMMA bone cement impregnated with antibiotic, which will fit within the implant area such that little or no space exists between the pre-formed temporary prosthesis and the surrounding tissue. The surgeon then inserts the selected prosthesis in the implant area, ensuring that the prosthesis occupies substantially the entire acetabular cavity such that the joint spacing will be maintained.

In an alternative method, the surgeon is provided with several prosthesis frames of various sizes. Once the size of the joint spacing has been determined, the surgeon selects an appropriately sized frame and fills recesses provided on the frame with an antibiotic-impregnated hardenable material such as PMMA bone cement. The recesses are filled to the point at which the hardenable material is flush with the outer edges of the prosthesis frame flanges such that a temporary non-weight bearing prosthesis is formed. Once the bone cement adequately hardens, the newly formed prosthesis is inserted into the implant area.

In another alternative method, the surgeon is provided with several of prosthesis molds adapted to form prostheses of various sizes to accommodate variously sized patients. As with the previously described methods, the surgeon first determines what size temporary prosthesis is needed. Once this is accomplished, the surgeon selects the appropriate mold and fills it with a hardenable material, such as PMMA, together with an antibiotic agent. When the hardenable material has adequately cured, the newly formed temporary prosthesis is inserted into the body in the manner described above.

Thus, it is an object of this invention to provide a pre-formed temporary hip prosthesis that is composed of a material impregnated with an antibiotic agent.

Another object of this invention is to provide a prosthesis frame having a plurality of recesses formed therein which are designed to be filled with an antibiotic-impregnated hardenable material such that a temporary prosthesis can be formed.

A further object of this invention is to provide a method of preventing the spread of infection while simultaneously maintaining joint spacing in an implant area of a hip replacement patient including the step of inserting a pre-formed temporary hip prosthesis composed of antibiotic-impregnated material.

Yet another object of this invention is to provide a method of preventing the spread of infection while simultaneously maintaining joint spacing in an implant area of a joint replacement patient including the step of applying antibiotic-impregnated hardenable material in recesses provided in a prosthesis frame such that a temporary prosthesis is formed.

A further object of this invention is to provide a method of preventing the spread of infection while simultaneously maintaining joint spacing in an implant area of a joint replacement patient including the step of filling a prosthesis mold with an antibioticimpregnated hardenable material such that a temporary prosthesis is formed.

Other objects, features and advantages of the present invention, will become apparent upon reading the following detailed description, when taken in conjunction with the accompanying drawings.

DESCRIPTION OF THE PREFERRED EMBODIMENTS

Figures 1, 2, 3:
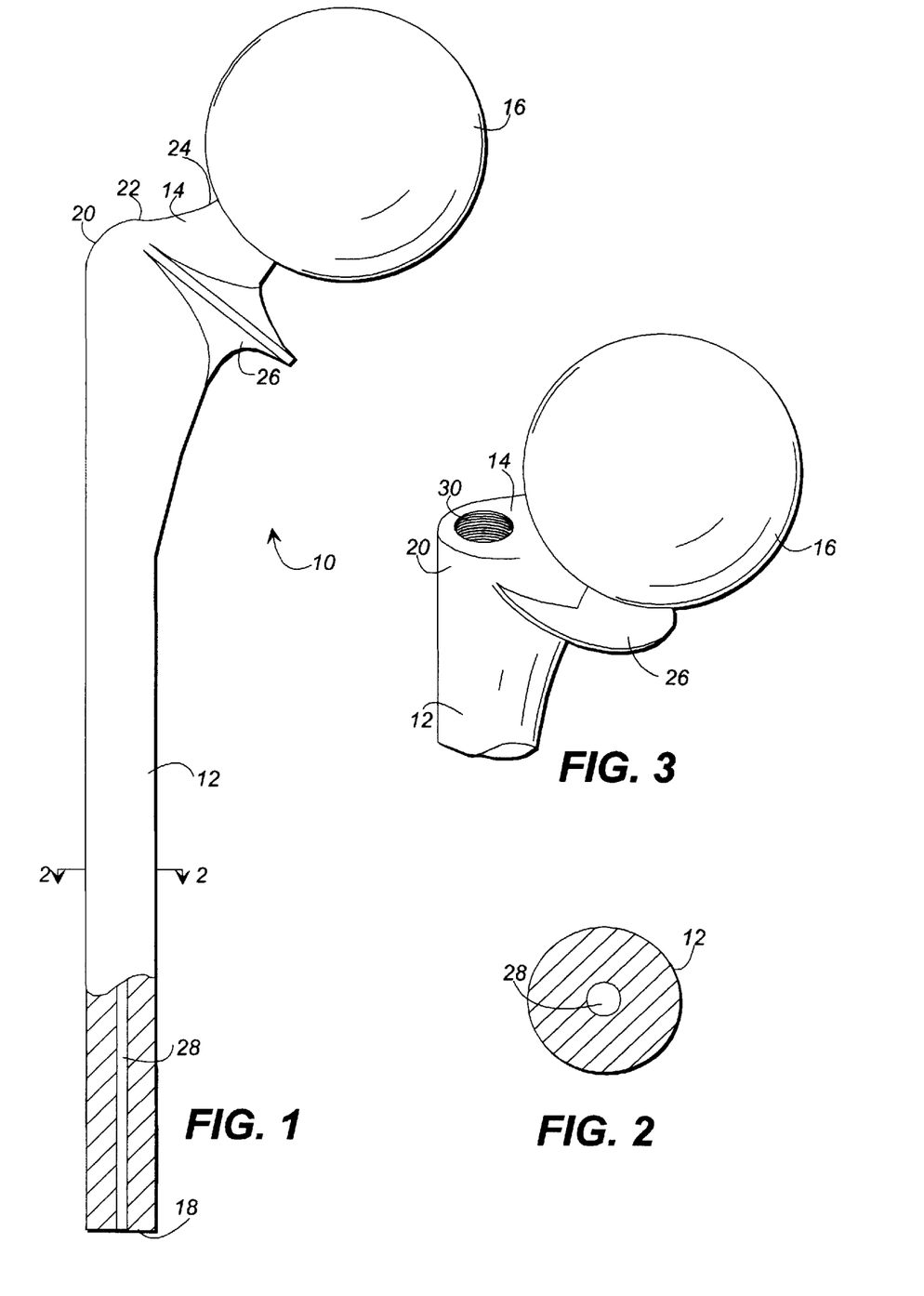
FIG. 1 illustrates a side elevational view, partially in section of a pre-formed temporary hip prosthesis of the present invention.
FIG. 2 illustrates a cross-sectional view of an elongated stem portion of the pre-formed temporary hip prosthesis illustrated in FIG. 1.
FIG. 3 illustrates an elevated perspective view of a threaded aperture of an alternative embodiment of the pre-formed temporary hip prosthesis.

Referring now in greater detail to the drawings in which like numerals indicate like parts throughout the several views, FIG. 1 illustrates the pre-formed temporary hip prosthesis 10 to be inserted in place of a primary hip prosthesis of a total hip stem replacement patient. As shown in the figure, the pre-formed temporary hip prosthesis 10 comprises an elongated stem portion 12, a neck portion 14, and a head portion 16. The elongated stem portion 12 is typically substantially cylindrical and has a lower distal end 18 and an upper proximal end 20. It will be understood, however, that the elongated stem portion may be formed in other shapes. Where the shape selected is cylindrical, the elongated stem portion 12 may be tapered along its length and usually will have a substantially circular cross-section as depicted in FIG. 2.

Similar to the elongated stem portion 12, the neck portion 14 has a lower distal end 22 and an upper proximal end 24. As shown most clearly in FIG. 1, the neck portion 14 extends from the upper proximal end 20 of the elongated stem portion 12 at an angle to simulate the shape and configuration of a human femur. The neck portion 14 may be formed substantially cylindrically as indicated in FIG. 1 or may take any other shape which would substantially simulate the function of a human femur.

As further illustrated in FIG. 1, the head portion 16 is formed on the upper proximal end 24 of the neck portion 14. Typically, the head portion 16 is substantially spherical, forming a bulbous head which simulates a femoral head of a human femur. It is to be understood, however, that the head portion could be formed in any shape which would adequately fill the patient's acetabular cavity to maintain the joint spacing of the implant area.

Typically, the pre-formed temporary hip prosthesis 10 will include a collar 26 formed at the juncture of the neck portion 14 and the elongated stem portion 12. In the preferred embodiment, the collar 26 is substantially disk-shaped and forms an acute angle with respect to the elongated stem portion 12 as depicted in FIG. 1.

As shown in FIGS. 1 and 2, the pre-formed temporary hip prosthesis 10 can also be cannulated, i.e., provided with an elongated canal 28 which is adapted to accept an elongated removal tool 32, described in more detail below, to facilitate removal of the temporary hip prosthesis from the body. The elongated canal 28 extends from the upper proximal end 20 to the lower distal end 18 of the elongated stem portion. As illustrated in FIG. 2, the elongated canal 28 may be a substantially cylindrical aperture formed concentrically with the elongated stem portion 12.

Illustrated in FIG. 3, the pre-formed temporary hip prosthesis may be provided with a threaded aperture 30 in the upper portion 20 of the elongated stem portion 12 in exception to or in addition to the elongated canal 28. The threaded aperture 30 is dimensioned and configured to accept a threaded removal tool 38, discussed in more detail below, which may be used to facilitate removal of the pre-formed temporary hip prosthesis.

In a preferred embodiment, each of the elongated stem portion 12, neck portion 14, and head portion 16 is composed of a bone cement such as polymethylmethacrylate ("PMMA"), commonly referred to as methylmethacrylate. These portions may be formed together in a single mold to form a one-piece temporary hip prosthesis or separately with each portion being connected together at a later time. Accordingly, the pre-formed temporary hip prosthesis 14 may be unitary or modular. In either case, bone cement is preferred because it is approved by the FDA for implantation into the human body.

Regardless of the particular material chosen for fabrication of the pre-formed temporary hip prosthesis, the material will contain an antibiotic agent. It is currently anticipated that the antibiotic agent will be impregnated into the material by simply mixing in an appropriate amount of antibiotic with the constituent elements of the material during the formation process of the temporary hip prosthesis. However, it will be understood that other methods of impregnation may be used, for example, soaking a porous temporary hip prosthesis in a liquid antibiotic.

When it is determined that a joint replacement patient has contracted an infection, the physician must further determine if the primary prosthesis should be removed. If such removal is warranted, a surgeon will remove the entire prosthesis. Although specific reference will be made to the hip replacement patients, it will be understood that the general procedure described herein is applicable to all joint replacement patients.

In the case of a total hip replacement patient, removal will include the extraction of both the hip stem fixed within the canal of the femur and the acetabular cup fixed to the patient's pelvis. Once these components of the primary prosthesis have been removed, the surgeon will inspect the implant area to check for signs of infection and will determine the size and extent of the joint spacing of the patient. The magnitude of this spacing will vary with the size of the patient and with the size of the primary prosthesis which had previously occupied the implant area. After the size of the joint spacing has been ascertained, the physician may then select the correctly sized pre-formed temporary hip prosthesis for the particular patient. Typically, the physician will be provided with a variety of differently sized prostheses to more closely match the temporary hip prosthesis with the patient. In particular, the physician will have available several different sizes of stem portion diameters with which to choose from. Moreover, the physician will also be able to choose a pre-formed temporary hip prostheses having a desired concentration of antibiotic impregnated therein. To simplify the selection process, it is anticipated that each pre-formed temporary hip prosthesis will be prepackaged in a sterile packet or container having indicia or color coding indicating the size of the prosthesis contained therein and its antibiotic concentration.

Once the selected pre-formed temporary hip prosthesis has been removed from the packaging, it may be altered by the surgeon or surgical assistant to more closely correlate to the particular patient. Typically, the elongated stem portion will be approximately between 200 and 250 mm long and the head portion will have a radius approximately between 44 and 48 mm in length. Since the elongated stem portion is substantially longer than the typical primary prosthesis stem, the elongated stem portion most often will need to be trimmed so that the length of the stem portion measured from the collar approximates the depth of the femoral canal of the patient. Trimming may be accomplished by cutting the elongated stem portion with a common surgical tool such as a bone saw. Due to the heat formed during the cutting process, the opening of the elongated canal of the elongated stem portion typically will need to be reformed to remove any bone cement that has fused the opening shut. In that the head portion of the temporary prosthesis will be substantially larger than the typical femoral head of a primary prosthesis, it also may need to be reduced in size. However, since both the hip stem and the acetabular cup of the primary hip prosthesis will have been removed, it is anticipated that a large head portion will be needed to ensure that the full joint spacing is maintained. Accordingly, the surgeon may even need to increase the size of the head portion by adding on additional antibiotic-impregnated bone cement.

After the temporary hip prosthesis has been trimmed and/or reshaped, the temporary hip prosthesis is inserted into the implant area. Specifically, the elongated stem portion is inserted into the canal of the femur with the head portion placed in the acetabular cavity of the hip. Overinsertion into the femoral canal is prevented with the collar 26, this collar abutting the top surface of the femur when the temporary hip prosthesis is fully inserted. The collar furthermore prevents the temporary hip prosthesis from creeping down into the canal during the recuperation period against the contractive force of the patient's tightening muscles and tendons.

Once the insertion procedure has been completed, the joint will be immobilized with the patient being either bedridden or, at minimum, unable to put weight on the joint in which the temporary hip prosthesis is provided. It is important that the patient be prevented from placing weight on the joint in that the temporary hip prosthesis is typically formed exclusively from bone cement which is far more brittle than the metals conventially used in primary hip prostheses. However, it will be noted that the temporary hip prosthesis is strong enough to withstand the contraction of the surrounding muscles and tendons of the patient during the recuperation period. During this time, the temporary hip prosthesis will be left in place, with the antibiotic agent impregnated into the bone cement leaching out to the surrounding tissue, preventing the formation of the infection in the implant area or destroying the infection if it had already formed.

Once the physician is satisfied that the infection has been overcome, the preformed temporary hip prosthesis 10 may be removed. Although the temporary hip prosthesis is not fixed in place in the manner in which primary prostheses are, tissue growth in the femoral canal may create difficulty in removing the temporary hip prosthesis. In cases in which the temporary hip prosthesis is provided with an elongated canal 28, an elongated removal tool 32 such as that depicted in FIG. 9 may be used to aid in the removal process. As shown in the figure, the removal tool can, for instance, be in the form of an elongated shaft 33 having a handle 34 and split ends provided with hooks 36 which, when inserted into the canal, are biased to spring out at the lower distal end 18 of the elongated stem portion 12 when the elongated removal tool is passed therethrough to firmly engage the temporary hip prosthesis. Once secured in this manner, the surgeon can remove the prosthesis simply by pulling it out with the handle 34. Alternatively, in cases in which the temporary hip prosthesis 10 is provided with a threaded aperture 30 at the upper proximal end 20 of the elongated stem portion 12, the temporary hip prosthesis may be removed with the aid of the threaded removal tool 38 depicted in FIG. 10. As illustrated in the figure, the threaded tool 38 can, for instance, take the form of a threaded bolt 40 provided with a handle 42. To remove the temporary hip prosthesis 10, the threaded tool 38 is threaded into the threaded aperture 30 and then the temporary hip prosthesis is pulled out from the femur by pulling outwardly on the handle 38.

After the pre-formed temporary hip prosthesis has been removed, the femoral canal is then carefully cleaned with a lavage to ensure that no bone cement remains in the femur. At this point, a primary hip prosthesis may again be implanted in the patient's hip.

Although the above described pre-formed temporary hip prosthesis would function well to fight infection and maintain joint spacing in the implant area, approval has not yet issued from the FDA for the commercial manufacture of products formed of antibioticimpregnated bone cement. Accordingly, until such approval is obtained, an interim solution to the problem is needed. The second embodiment of the invention provides such a solution.

Figure 4:
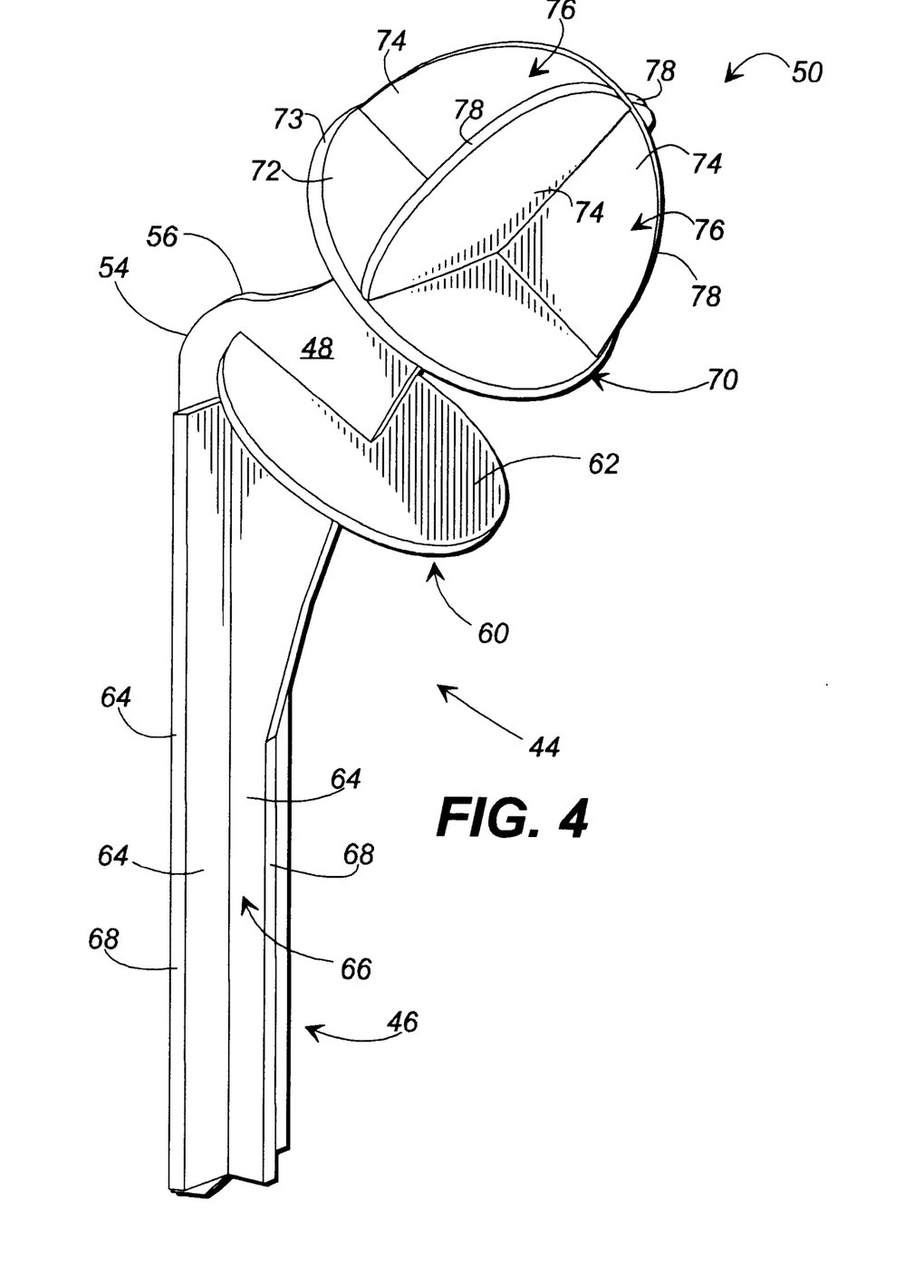
FIG. 4 illustrates a perspective view of a prosthesis frame of the present invention.
Figures 5, 6, 7:
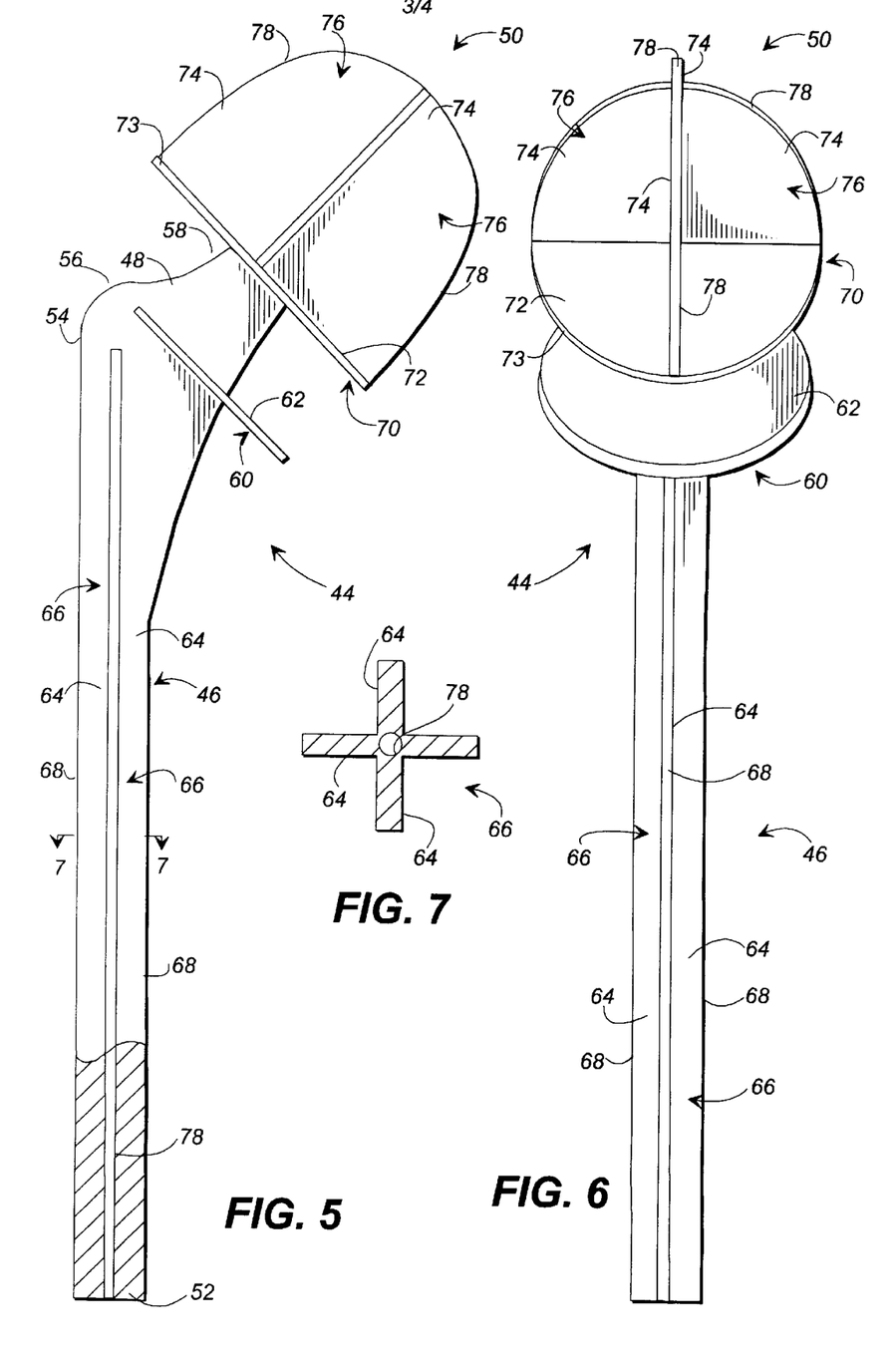
FIG. 5 illustrates a side elevational view of the prosthesis frame illustrated in FIG. 4.
FIG. 6 illustrates a front elevational view of the prosthesis frame.
FIG. 7 illustrates a cross-sectional view of an elongated stem portion of the prosthesis frame.

In another embodiment of the invention, the physician is provided with a prosthesis frame 44 such as that depicted in FIGS. 4–6. Although a hip prosthesis frame will be described, it is to be understood that the prosthesis frame could be provided to accommodate any joint in which joint replacement has been performed.

As illustrated in the figures, the hip prosthesis frame, similar to the pre-formed temporary hip prosthesis, comprises an elongated stem portion 46, a neck portion 48, and a head portion 50. Furthermore, the elongated stem portion 46 has a lower distal end 52 and an upper proximal end 54. Similarly, the neck portion 48 also has a lower distal end 56 and an upper proximal end 58, the neck portion 48 extending upwardly from the upper proximal end 54 of the elongated stem portion 46 at an angle to simulate the shape and configuration of a human femur. As shown in FIG. 5, the head portion 50 is connected to the upper proximal end 58 of the neck portion 48. In addition, the prosthesis frame 44 is provided with a collar 60 positioned at the juncture of the neck portion 48 and the elongated stem portion 46. Included on the collar 60 is an upper surface 62 which faces the head portion 50. Like the pre-formed temporary hip prosthesis, the prosthesis frame will typically be formed from bone cement.

Unlike the pre-formed temporary hip prosthesis 10, however, the elongated stem portion 46 of the prosthesis frame 44 is provided with a plurality of radial flanges 64 which extend from a central axis of the elongated stem portion. Although the elongated stem portion 46 is shown in FIGS. 4–7 as having four radial flanges 64, it is to be understood that any number of radial flanges could be provided. As shown in these figures, the radial flanges 64 extend substantially along the entire length of the elongated stem portion 46. Configured in this manner, the radial flanges 64 provide a plurality of elongated recesses 66 which extend from the central axis of the elongated stem portion 46 to the outer edges 68 of each radial flange 64. These elongated recesses 66 are adapted to receive and support a hardenable material, such as bone cement, which is impregnated with an antibiotic. Thus, the frame 44 functions as the endoskeleton for the end product, and the stem portion 46 functions as a stem support for the stem of the final product.

As illustrated in FIGS. 4–6, the head portion 50 comprises a substantially circular base portion 70 having a top surface 72 and an outer edge 73. Positioned atop the top surface 72 is a plurality of arcuate flange members 74 which extend upwardly from the top surface 72 and preferably meet along a central axis normal to the circular base portion 70. It is to be noted that although the head portion 50 is shown as having four flanges members 74, any number of flange members could be used. Similar to the radial flanges, the arcuate flange members 74 provide a plurality of recesses 76 which extend outwardly toward the outer edges of the circular base portion 70 and each arcuate flange member 74. Like those of the elongated stem portion, these recesses 76 are adapted to receive and support a hardenable material, such as bone cement, which is impregnated with an antibiotic. Therefore, the head portion 50 functions as a ball support, for supporting the final ball that is formed on the prosthesis frame, The prosthesis frame 44 may also be provided with means for facilitating its removal from the femoral cavity once the infection has been overcome. As illustrated in FIGS. 5 and 7, the elongated stem portion 46 of the prosthesis frame 44 typically is provided with an elongated canal 78 which extends from the upper proximal end 54 to the lower distal end 52 of the elongated stem portion 46. Although it is preferable to provide the prosthesis stem portion with such a canal, the prosthesis frame could alternatively be provided with a threaded metal sleeve (not shown) placed in the upper proximal end 54 of the elongated stem portion 46 which would provide a threaded aperture similar to threaded aperture 30 of the pre-formed temporary hip prosthesis 10 described above.

Figures 8, 9, 10:
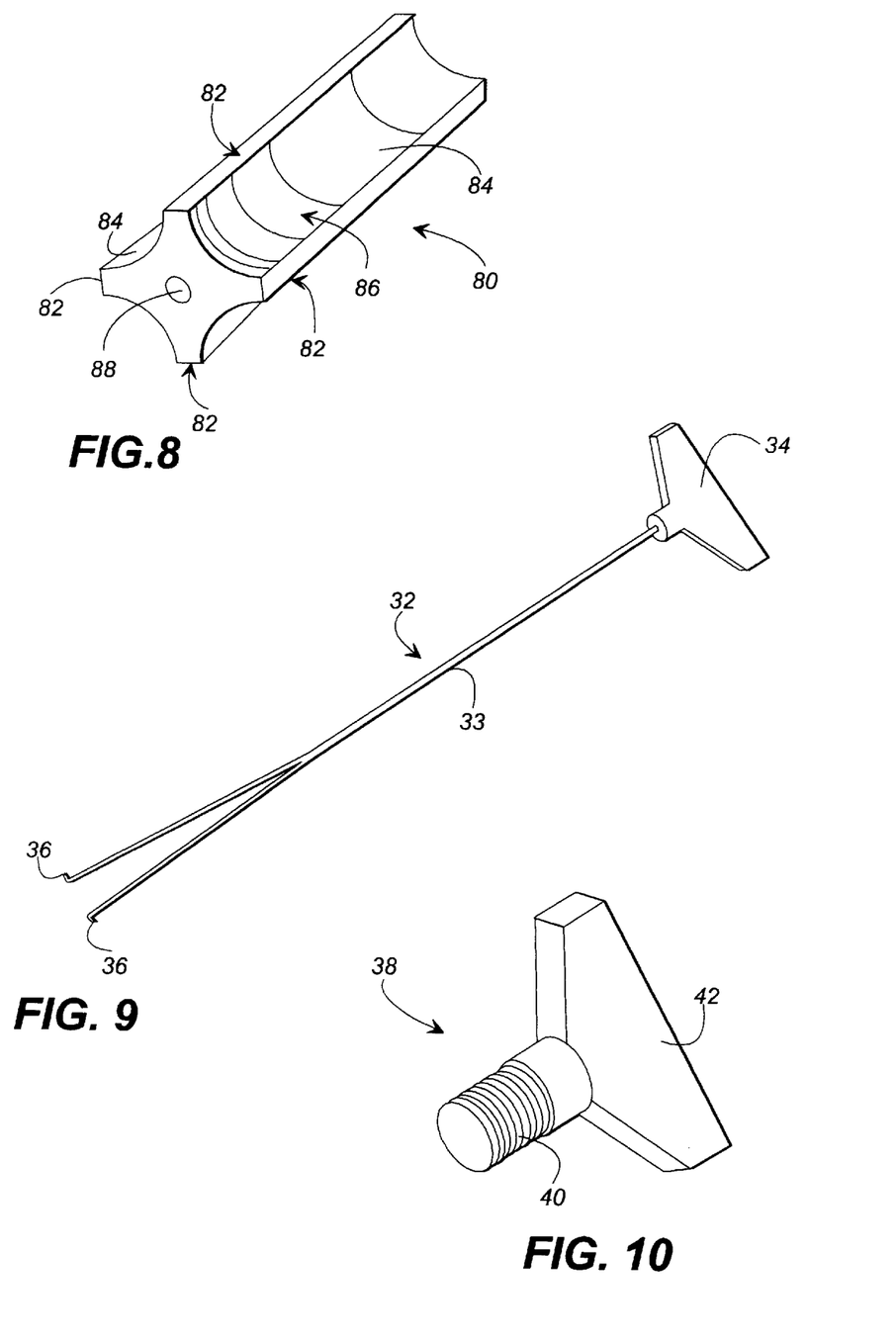
FIG. 8 illustrates an elevated perspective view of an alternative configuration of the elongated stem portion of the prosthesis frame.
FIG. 9 illustrates a perspective view of an elongated removal tool.
FIG. 10 illustrates a perspective view of threaded removal tool.

FIG. 8 depicts an alternative arrangement of the elongated stem portion 46 of the prosthesis frame 44. In this embodiment, the elongated stem portion 80 is provided with curved radial flanges 82 formed from concave channels 84 extending along the length of the elongated stem portion 80 such that the elongated stem portion has a substantially star-shaped cross-section. Each of the concave channels 84 provide elongated recesses 86 which, similar to the above described recesses, may be filled with antibiotic-impregnated bone cement. As with the first configuration of the elongated stem portion of the prosthesis frame, the alternative elongated stem portion 80 may also be provided with an elongated canal 88 or a threaded sleeve (not shown) to facilitate removal of the temporary prosthesis after the infection has been overcome. Although not depicted in the figures, the arcuate flange members 74 of the head portion 50 may likewise be formed from concave surfaces. When the frame is formed with curved radial flanges and curved arcuate flange members as described above, less antibiotic-impregnated hardenable material and less time will be required to form the temporary prosthesis.

The prosthesis frame is used in a manner similar to that of the pre-formed temporary hip prosthesis. When it is determined that a joint implant must be removed due to infection, the physician will remove the entire prosthesis and inspect the implant area to determine the size and extent of the joint spacing of the patient. After the size of the joint spacing has been ascertained, the physician then selects a prosthesis frame appropriate for the particular application. It is anticipated that only one size prosthesis frame will be required for each application whether it be a hip stem prosthesis frame, knee prosthesis frame, or otherwise. It will be understood, however, that a variety of differently sized prostheses could be made available to the physician to more closely match the particular patient. Like the pre-formed temporary hip prosthesis described above, each prosthesis frame will be pre-packaged in a sterile packet or container having indicia or color coding which indicates the size and antibiotic concentration of the prosthesis contained therein.

Once the appropriate prosthesis frame has been selected, it may be altered by the surgeon or surgical assistant to more closely correlate to the particular patient. In the case of a hip prosthesis frame described above, the elongated stem portion will be approximately between 200 and 250 mm long and the outer edges of the circular base portion 70 and the arcuate flanges 74 will form the outline of a semi-sphere having a radius approximately between 44 and 48 mm in length. Most often, the elongated stem portion will need to be trimmed so that the length of the stem portion approximates the depth of the femoral canal of the patient. Where the prosthesis frame is provided with an elongated canal, the opening of the canal may need to be reformed due to fusion of the opening resulting from heat formed during the cutting process.

After the temporary hip prosthesis has been trimmed, an antibiotic-impregnated hardenable material can be applied to the recesses 66 and 76 of the prosthesis frame. The hardenable material, preferably PMMA bone cement, is liberally applied in the recesses 66 and 76 until it is substantially flush with the outer edges of the radial flanges, the circular base portion, and the arcuate flange members, thereby forming a temporary hip prosthesis having a substantially cylindrical shank and a substantially bulbous head. In addition, the neck portion of the frame between the collar and the base portion may also be provided with antibiotic-impregnated bone cement if desired.

Once the hardenable material has adequately cured, the newly formed temporary hip prosthesis, or other non-weight bearing temporary prosthesis, is inserted into the implant area. Next, the limb will be immobilized to prevent the patient from putting weight on the joint. As with the pre-formed temporary hip prosthesis, the temporary prosthesis formed from the prosthesis frame will be left in place for several weeks during which time the antibiotic will leach out to the surrounding tissue to destroy the infection. Once the infection has been eradicated, the temporary prosthesis may be removed. In cases where the temporary prosthesis is a hip prosthesis provided with an elongated canal 78 or 88, an elongated removal tool 32 similar to that depicted in FIG. 9 may be used to aid in the removal process. Alternatively, in cases in which the temporary hip prosthesis is provided with a threaded sleeve at the upper proximal end 54 of the elongated stem portion, the temporary hip prosthesis may be removed with the aid of the threaded removal tool 38 depicted in FIG. 10.

In an alternative method of fighting infection and maintaining joint spacing in an implant area, a temporary prosthesis is formed by the surgeon with the use of a prosthesis mold. After the size of the joint spacing has been ascertained, the surgeon or a surgical assistant selects a prosthesis mold which is configured to produce a temporary prosthesis of a size appropriate for the particular infected patient. It is anticipated that a variety of differently sized prosthesis molds could be made available to the surgical staff to closely match the patient's anatomy. Once the appropriate prosthesis mold has been selected, the surgeon or surgical assistant mixes the hardenable material with a predetermined amount of antibiotic and fills the mold such that the entire inner space of the mold is occupied with antibiotic-impregnated hardenable material. Once the material has adequately hardened, the newly formed temporary prosthesis may be removed and shaped if necessary to accommodate the implant patient. At this point, the temporary prosthesis is inserted into the implant area in accordance with the above described methods.

In light of the above, it will be appreciated that the present invention provides methods and apparatus for fighting infection and maintaining joint spacing in an implant area of a joint replacement patient with great advantages over the prior art. While the forgoing invention has been described in the form of preferred embodiments and procedures, it will be understood by those skilled in the art that numerous modifications, variations, and changes, can be made thereto without departure from the spirit and scope of the invention as set forth in the following claims.

I claim:

1. A method of preventing the spread of infection and maintaining joint spacing in an implant area of a hip replacement patient, the method comprising the steps of:

examining the implant area to determine the size and extent of the joint spacing;

selecting a pre-formed temporary hip prosthesis composed of antibiotic-impregnated material and sized to fit within the implant area such that, once inserted within the implant area, little or no space is left between said pre-formed temporary hip prosthesis and the surrounding tissue of the implant area, said pre-formed temporary hip prosthesis having an elongated stem, a neck portion, and a head, each of said elongated stem, neck portion, and head being composed of said antibiotic-impregnated material;

inserting said pre-formed temporary hip prosthesis into the implant area with said elongated stem inserted into the femoral cavity and said head occupying the acetabular cavity such that the antibiotic can leach out of said antibiotic-impregnated material to fight infection and said neck portion and said head can maintain adequate joint spacing in opposition to contraction of the muscles and tendons of the patient; and removing said pre-formed temporary hip prosthesis from the implant area once the infection has been overcome so that a primary prosthesis can be implanted into the implant area after the infection has been overcome.

2. The method of claim 1, wherein said antibiotic-impregnated material is polymethylmethacrylate.

3. The method of claim 2 further comprising the step of shortening the length of said elongated stem before said pre-formed temporary hip prosthesis is inserted into the implant area so that the length of said elongated stem closely matches the depth of the femoral cavity of the patient.

4. A method of preventing the spread of infection and maintaining joint spacing in an implant area of a hip replacement patient, the method comprising the steps of:

examining the implant area to determine the size and extent of the joint spacing;

selecting a pre-formed temporary hip prosthesis composed of antibiotic-impregnated material and sized to fit within the implant area such that, once inserted within the implant area, little or no space is left between said pre-formed temporary hip prosthesis and the surrounding tissue of the implant area, said pre-formed temporary hip prosthesis having an elongated stem, a neck portion, and a head, each of said elongated stem, neck portion, and head being composed of said antibiotic-impregnated material;

inserting said pre-formed temporary hip prosthesis into the implant area with said elongated stem inserted into the femoral cavity and said head occupying the acetabular cavity such that the antibiotic can leach out of said antibiotic-impregnated material to fight infection and said head can maintain adequate joint spacing in opposition to contraction of the muscles and tendons of the patient so that a primary prosthesis can be implanted into the implant area after the infection has been overcome, and removing said pre-formed temporary hip prosthesis from the implant area once the infection has been overcome by inserting an elongated removal tool through a canal provided through said elongated stem until the elongated removal tool grips a lower distal end of said elongated stem, and pulling said elongated stem out of the femoral cavity of the patient with the elongated removal tool.

5. The method of claim 2, wherein the step of removing said temporary hip prosthesis from the implant area once the infection has been overcome is accomplished by threading a removal tool into a threaded aperture formed in an upper proximal end of said elongated stem, and pulling said elongated stem out of the femoral cavity of the patient with the removal tool.

6. A method of preventing the spread of infection and maintaining joint spacing in an implant area of a joint replacement patient, the method comprising the steps of:

examining the implant area to determine the size and extent of the joint spacing;

selecting a prosthesis frame sized to fit within the implant area, said prosthesis frame having a plurality of recesses provided thereon;

applying an antibiotic-impregnated hardenable material into said recesses provided on said prosthesis frame until forming a temporary prosthesis sized to fit within the implant area such that, once inserted within the implant area, little or no space is left between said temporary prosthesis and the surrounding tissue of the implant area;

permitting said antibiotic-impregnated hardenable material in said recesses of said temporary prosthesis to harden;

inserting said temporary prosthesis into the implant area such that the antibiotic can leach out of said hardened material to fight infection and said temporary prosthesis can maintain adequate joint spacing in opposition to contraction of the muscles and tendons of the patient; and removing said temporary hip prosthesis from said implant area once the infection has been overcome so that a primary prosthesis can be implanted into the implant area after the infection has been overcome.

7. The method of claim 6, wherein said hardenable material is polymethylmethacrylate.

8. The method of claim 7 wherein said temporary prosthesis is a temporary hip prosthesis, the method further comprising the step of shortening the length of an elongated stem of said temporary hip prosthesis before said temporary hip prosthesis is inserted into the implant area so that the length of said elongated stem closely matches the depth of the femoral cavity of the patient.

9. A method of preventing the spread of infection and maintaining joint spacing in an implant area of a joint replacement patient the method comprising the steps of:

examining the implant area to determine the size and extent of the joint spacing;

selecting a prosthesis frame sized to fit within the implant area said prosthesis frame having a plurality of recesses provided thereon;

applying an antibiotic-impregnated hardenable material into said recesses provided on said prosthesis frame until forming a temporary prosthesis sized to fit within the implant area such that, once inserted within the implant area, little or no space is left between said temporary prosthesis and the surrounding tissue of the implant area;

permitting said antibiotic-impregnated hardenable material in said recesses of said temporary prosthesis to harden;

inserting said temporary prosthesis into the implant area such that the antibiotic can leach out of said hardened material to fight infection and said temporary prosthesis can maintain adequate joint spacing in opposition to contraction of the muscles and tendons of the patient so that a primary prosthesis can be implanted into the implant area after the infection has been overcome; and removing said temporary hip prosthesis from said implant area once the infection has been overcome by inserting an elongated removal tool through a canal provided through said elongated stem until the elongated removal tool grips a lower distal end of said elongated stem, and pulling said elongated stem out of the femoral cavity of the patient with the elongated removal tool.

10. The method of claim 8 wherein the step of removing said temporary hip prosthesis from said implant area once the infection has been overcome is accomplished by threading a removal tool into a threaded aperture formed in an upper proximal end of said elongated stem, and pulling said elongated stem out of the femoral cavity of the patient with the removal tool.

* * * * *